United States Patent [19]

Kim

[11] Patent Number: 5,015,737

[45] Date of Patent: May 14, 1991

[54] THERAPEUTICALLY USEFUL BETA-LACTAMS

[75] Inventor: Kyoung S. Kim, Kalamazoo, Mich.

[73] Assignee: The Upjohn Company, Kalamazoo, Mich.

[21] Appl. No.: 460,840

[22] PCT Filed: Jul. 6, 1988

[86] PCT No.: PCT/US88/02197

§ 371 Date: Jan. 25, 1990

§ 102(e) Date: Jan. 25, 1990

[87] PCT Pub. No.: WO89/00569

PCT Pub. Date: Jan. 26, 1989

Related U.S. Application Data

[63] Continuation-in-part of Ser. No. 76,502, Jul. 22, 1987, abandoned.

[51] Int. Cl.$^5$ .................. A61K 31/64; C07D 401/14; C07D 417/14
[52] U.S. Cl. ..................... 540/363; 540/364
[58] Field of Search ................. 540/363, 364

[56] References Cited

U.S. PATENT DOCUMENTS 4,587,047 5/1986 Breuer .................. 540/357
4,670,553 6/1987 Breuer .................. 540/363

FOREIGN PATENT DOCUMENTS 905502A   1/1987  Belgium .
0053815  12/1981  European Pat. Off. .
0053816  12/1981  European Pat. Off. .
0076758  10/1982  European Pat. Off. .
0085291  10/1983  European Pat. Off. .
0096297  12/1983  European Pat. Off. .
0114128   7/1984  European Pat. Off. .
2181130   4/1987  United Kingdom .

OTHER PUBLICATIONS

Breuer, H., et al., Abstract 371, Sep. 29–Oct. 2, 1985, XXV Interscience Conference on Antimicrobial Agents and Chemotherapy, Minneapolis, Minnesota.
Tanaka, S. K., et al., Abstract 372, Sep. 29–Oct. 2, 1985, XXV Interscience Conference on Antimicrobial Agents and Chemotherapy, Minneapolis, Minnesota.
Clark, J. M., et al., Abstract 373, Sep. 29–Oct. 2, 1985, XXV Interscience Conference on Antimicrobial Agents and Chemotherapy, Minneapolis, Minnesota.
Breuer, H., et al., Abstract 847, Sep. 28–Oct. 1, 1986, XXVI Interscience Conference on Antimicrobial Agents and Chemotherapy, New Orleans, Louisiana.
Whitney, R. R., et al., Abstract 848, Sep. 28–Oct. 1, 1986, XXVI Interscience Conference on Antimicrobial Agents and Chemotherapy, New Orleans, Louisiana.
Pilkiewicz, F. G. and Bemsburg, B. J., Abstract 849, Sep. 28–Oct. 1, 1986, XXVI Interscience Conference on Antimicrobial Agents and Chemotherapy, New Orleans, Louisiana.

Primary Examiner—Mark L. Berch
Attorney, Agent, or Firm—Paul W. Busse; Donald L. Corneglio

[57] ABSTRACT

This invention presents novel 2-azetidinone compounds of the formula

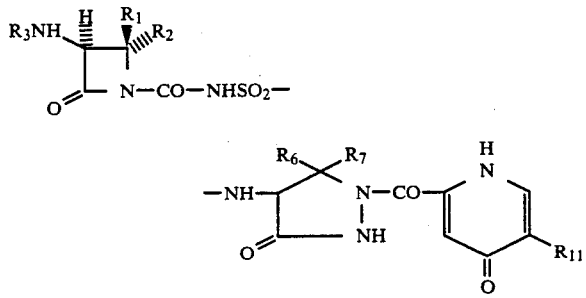

wherein $R_1$ and $R_2$ are the same or different and are hydrogen ($C_1$–$C_{12}$) alkyl, ($C_2$–$C_8$) alkenyl, ($C_2$–$C_8$) alkynyl, ($C_3$–$C_{10}$) cycloalkyl, phenyl optionally substituted with from one to 3 substituents selected from the group consisting of halogen, hydroxy, amino, nitro, ($C_1$–$C_4$)alkyl, and ($C_1$–$C_4$)alkoxy, benzyl optionally subsituted with from one to 3 substituents selected from the group consisting of halogen, hydroxy, amino, nitro, ($C_1$–$C_4$)alkyl, and ($C_1$–$C_4$)alkoxy, —CH$_2$—O—CO—CH$_2$—NHR$_4$, —CH$_2$—O—CO$_2$—R$_5$, —CH$_2$F, or —CHF$_2$; wherein $R_4$ is hydrogen, —CHO or —CO—O—C(CH$_3$)$_3$; wherein $R_5$ is —($C_1$–$C_8$)alkyl, —(CH$_2$)$_2$NH—CO—O—C(CH$_3$)$_3$, —(CH$_2$)$_2$N(CH$_3$)—CO—O—C(CH$_3$)$_3$, —(CH$_2$)$_2$OC(O)NH$_2$, —(CH$_2$)$_2$Cl, —(CH$_2$)$_2$OCH$_3$ or —(CH$_2$)$_2$NHCHO; wherein $R_3$ is an acyl group derived from a carboxylic acid; wherein $R_6$ is hydrogen or methyl; wherein $R_7$ is hydrogen or methyl; wherein $R_{11}$ is hydroxy or —O—CH$_2$—($C_6$H$_5$); with the proviso that $R_6$ and $R_7$ cannot both be methyl.

These compounds have an activating group which contains a chiral pyrazolidinone moiety and are useful as antibacterial agents.

6 Claims, No Drawings

1

THERAPEUTICALLY USEFUL BETA-LACTAMS

This is a C.I.P. of 07/076,502, filed July 22, 1987, now abandoned.

FIELD OF THE INVENTION

This invention encompasses novel 2-azetidinone compounds containing chiral aminopyrazolidinones which have useful antimicrobial activity.

INFORMATION DISCLOSURE

Derivatives of 2-azetidinone which have antimicrobial and β-lactamase inhibitory activity are known in the art European Patent Applications 0053815, 0053816, 0076758 and 0096297 disclose β-lactams with various substituents at the C4 position of the ring.

European Patent Application 0053816 discloses 2-azetidinone compounds substituted at the C4 position with an organic residue. However, the documents do not suggest the specific substituents disclosed herein and do not suggest or teach how to make the specific compounds of this application.

Abstracts from papers presented by Squibb Institute for Medical Research at the 25th and 26th Interscience Conferences on Antimicrobial Agents and Chemotherapy disclose antibacterial substituted sulfonylaminocarbonyl-2-azetidinones containing a substituted heterocycle in the sulfonylaminocarbonyl activating group at the N-1 position and a 2-(2-amino-4-thiazolyl)-2-(1-carboxy-1-methylethoxy)-iminoacetamido group at the C3 position.

U.S. Pat. No. 4,587,047, filed Apr. 1, 1982, issued May 6, 1986, discloses substituted sulfonylaminocarbonyl-2-azetidinones. U.S. patent application Ser. No. 444,771 filed Nov. 26, 1982, and European Patent Application No. 0085291, filed Mar. 1, 1983, published Oct. 8, 1983 disclose substituted sulfonylaminocarbonyl-2-azetidinones containing a substituted heterocycle in the sulfonylaminocarbonl activating group. U.K. Patent Application No. 8623151, filed Sept. 26, 1986, and Belgium Patent 905502A disclose sulfonylaminocarbonyl-2-azetidinones containing an imidazolidonylaminocarbonyl-2(1,4-dihydro-5-hydroxy4-oxo)pyridine in the activating group. None of the above documents discloses a substituted sulfonylaminocarbonyl-2-azetidinone which has a chiral aminopyrazolidinone in the activating group.

SUMMARY OF THE INVENTION

The present invention teaches novel 2-azetidinone analogs containing chiral aminopyrazolidinones which are useful as microbial growth inhibitors. This invention includes enantiomers, diastereomeric and racemic mixtures of these compounds. Intermediates and processes for preparing these compounds are also disclosed Novel 2-azetidinone analogs within the scope of this invention are represented by Formula I and pharmaceutically acceptable salts thereof.
wherein $R_1$ and $R_2$ are the same or different and are
a) hydrogen
b) $(C_1-C_{12})$ alkyl,
c) $(C_2-C_8)$ alkenyl,
d) $(C_2-C_8)$ alkynyl,
e) $(C_3-C_{10})$ cycloalkyl,
f) phenyl optionally substituted with from one to 3 substituents selected from the group consisting of halogen, hydroxy, amino, nitro, $(C_1-C_4)$alkyl, and $(C_1-C_4)$alkoxy.
g) benzyl optionally substituted with from one to 3 substituents selected from the group consisting of halogen, hydroxy, amino, nitro, $(C_1-C_4)$alkyl, and $(C_1-C_4)$alkoxy,
h) $-CH_2-O-CO-CH_2-NHR_4$,
i) $-CH_2-O-CO_2-R_5$,
j) $-CH_2F$, or
k) $-CHF_2$;
wherein $R_4$ is hydrogen, $-CHO$, or $-CO-O-C(CH_3)_3$;
wherein $R_5$ is $-(C_1-C_8)$alkyl, $-(CH_2)_2-NH-CO-O-C(CH_3)_3$, $-(CH_2)_2-N(CH_3)-CO-O-C(CH_3)_3$, $-(CH_2)_2OC(O)NH_2$, $-(CH_2)_2Cl$, $-(CH_2)_2OCH_3$ or- $(CH_2)_2NHCHO$;
wherein $R_3$ is an acyl group derived from a carboxylic acid;
wherein $R_{60}$ is a pyrazolidinone represented by Formula II;
wherein $R_6$ and $R_7$ are hydrogen or methyl;
wherein $R_7$ is hydrogen or methyl;
wherein $R_{11}$ is hydroxy or $-O-CH_2-(C_6H_5)$;
with the proviso that $R_6$ and $R_7$ cannot both be methyl.

Novel compounds within the scope of this invention which are useful as intermediates to 2-azetidinone analogs having microbial growth inhibition include compounds of Formula I wherein $R_4$ is $-CHO$ and $-CO-O-C(CH_3)_3$; wherein $R_5$ is $-(CH_2)_2-NH-CO-O-C(CH_3)_3$, $-(CH_2)_2-N(CH_3)-CO-O-C(CH_3)_3$ and wherein $R_{11}$ is $-O-CH_2-(C_6H_5)$.

A detailed description of the acyl groups included in $R_3$ is found in U.S. Pat. No. 4,478,749, column 8, line 41, to column 12, line 50, as those terms are defined at column 7, line 34 through column 8, line 22, all of which is incorporated by reference herein.

Preferred acyl groups of $R_3$ include those which have been used to acylate 6-aminopenicillanic acid, 7-aminocephalosporic acid and their derivatives which can be found in "Chemistry and Biology of β-Lactam Antibiotics Vol. 1, R. B. Morin and M. Gorham, ed., Academic Press, N.Y. 1982 and include the following list: 2-Cyanoacetyl, Aminophenylacetyl Amino(4-hydroxyphenyl)acetyl, α(Thien-2-yl)acetyl, α(Thien-3-yl)acetyl, Phenylacetyl, Hydroxyphenylacetyl (Formyloxy)-phenylacetyl, [(Trifluoromethyl)thio]acetyl, 2-(3,5-Dichloro-4-oxo-1-(4H)-pyridyl)acetyl, (1H-Tetrazol-1-yl)acetyl (2-Amino-4-thiazolyl)-2-methoxyiminoacetyl, 2-[(Cyanomethyl)thio]acetyl, [[(4-Ethyl-2,3-dioxo-1-piperizinyl)carbonyl]amino]phenylacetyl, [[(4-Ethyl-2,3-dioxo-piperazinyl)carbonyl]amino](4-hydroxyphenyl)acetyl, 2-(Aminomethyl)phenylacetyl, 4-(Carbamoylcarboxymethylene)-1,3-dithiethane-2-carbonyl, 3-(o-Chlorophenyl)-5-methyl-4-isoxazolecarbonyl, 2-p-[(1,4,5,6-Tetrahydro-2-pyrimidinyl)phenyl]acetyl, Amino-1,4-cyclohexadien-1-yl-acetyl, Phenylsulfoacetyl, (2R)-2-amino-2-(m-methanesulfonamidophenyl)acetyl, (2-Amino-4-thiazolyl)-2-(1-carboxy-1-methylethoxy)iminoacetyl 2-(1H-Tetrazol-1-yl)acetyl (2,3-Dihydro-2-imino-4-thiazolyl)(methoxyimino)acetyl, (2-Amino-4-thiazol)carboxymethoxyiminoacetyl, (2-Aminopyridin-6-yl)methoxyiminoacetyl, (2-Aminopyridin-6-yl)carboxymethoxyiminoacetyl (4-Amino-2-pyrimidyl)methoxyiminoacetyl, (5-Amino-1,2,4, -thiadiazol-3-yl)-2-methoxyiminoacetyl, (5-Amino-1,2,4-thiadiazol-3-yl)-2-carboxymethoxyiminoacetyl, (5-Amino-1,2,4-thiadiazol-3-yl)-1-carboxy-1- methylethoxy)iminoacetyl, D-α[[(Imidazolidin-2-on-1--yl)-carbonyl]amino]phenylacetyl, D-α[[(3-mesyl-imidazolidin-2-on-1-yl)carbonyl]amino]phenylacetyl, 2,6-Dimethylbenzoyl, (S)-2-(4-hydroxy-1,5-naphthyridine-3-carboxamido-2-phenylacetyl.

Preferred compounds within the scope of this invention include compounds wherein the organic acid derivative, $R_3$, is an oximinoacyl moiety represented by Formula III;
wherein $R_8$ is
a) $-CH_3$,
b) $-CH_2-CO_2-R_9$,
c) $-C(CH_3)_2-CO_2-R_9$,
d) $-CH(CH_3)-CO_2-R_9$,
e) $-C(CH_2)-CO_2-R_9$,
f) $X_1-CO_2-R_9$,
g) $-CH_2-CO-NHOH$, or
h) $-C(CH_3)_2-CO-NHOH$;
wherein $X_1$ is 1,1-cyclopropylidene; 1,2-cyclopropylene, 1,1-cyclobutylidene, 1,2-cyclobutylene, 1,3-cyclobutylene, 1,1,-cyclopentylidene, 1,2,-cyclopentylene or 1,3-cyclopentylene; wherein $R_9$ is
a) hydrogen;
b) ($C_1-C_4$) alkyl,
c) $-CH(C_6H_5)2$,
d) $-CH_2(C_6H_5)$, or
e) a cation;
wherein $R_{10}$ is
a) hydrogen,
b) 13 $CO-O-C(CH_3)_3$,
c) $-CO-O-CH_2-(C_6H_5)$, or
d) $-C(C_6H_5)_3$.

Novel compounds within the scope of this invention containing an oximinoacyl moiety represented by Formula III which are useful as intermediates to 2-azetidinone analogs having microbial growth inhibition include compounds wherein $R_9$ is ($C_1-C_4$) alkyl, $-CH(C_6H_5)_2$, or $-CH_2(C_6H_5)$; and wherein $R_{10}$ is $-CO-O-C(CH_3)_3$, $-CO-O-CH_2-(C_6H_5)$, or $-C(C_6H_5)_3$.

The compounds of this invention are identified in two ways: by the descriptive name and by numerical identification which corresponds to the appropriate structure contained in the structure charts. In appropriate situations, the proper stereochemistry is represented in the structure charts as well.

The various carbon moieties are defined as follows:
Alkyl refers to an aliphatic hydrocarbon radical and includes branched or unbranched forms such as methyl, ethyl, n-propyl, isopropyl n-butyl, isobutyl, sec-butyl, t-butyl, n-pentyl isopentyl, neo-pentyl, n-hexyl, isohexyl, n-heptyl isoheptyl, n-octyl, isooctyl, n-nonyl, n-decyl, n-undecyl, and n-dodecyl.

Alkoxy refers to an alkyl radical which is attached to the remainder of the molecule by oxygen and includes branched or unbranched forms such as methoxy, ethoxy, n-propoxy, isopropoxy n-butoxy, iso-butoxy, sec-butoxy, and t-butoxy.

Alkenyl refers to a radical of an aliphatic unsaturated hydrocarbons having a double bond and includes both branched and unbranched forms such as ethenyl, 1-propenyl, 2-propenyl, 1-butenyl, 2-butenyl, 3-butenyl, 2-methyl-1-butenyl, 1-pentenyl, 2-pentenyl 3-pentenyl, 4-pentenyl, 1-methyl-4-pentenyl, 3-methyl-1-pentenyl, 3-methyl-2-pentenyl, 1-hexenyl, 2-hexenyl, 3-hexenyl, 4-hexenyl 1-methyl-4-hexenyl, 3-methyl-1-hexenyl, 3-methyl-2-hexenyl, 1-heptenyl, 2-heptenyl, 3-heptenyl 4-heptenyl, 1-methyl-4-heptenyl, 3-methyl-1-heptenyl, 3-methyl-2-heptenyl, 1-octenyl, 2-octenyl, or 3-octenyl.

Alkynyl refers to a radical of an aliphatic unsaturated hydrocarbons having a triple bond and includes both branched and unbranched forms such as ethynyl, 1-propynyl, 2-propynyl, 1-butynyl, 2-butynyl, 3-butynyl, 2-methyl-1-butynyl, 1-pentynyl, 2-pentynyl, 3-pentynyl, 4-pentynyl, 1-methyl-4-pentynyl, 3-methyl-1-pentynyl, 3-methyl 2-pentynyl, 1-hexynyl, 2-hexynyl, 3-hexynyl, 4-hexynyl, 1-methyl-4-hexynyl, 3-methyl-1-hexynyl, 3-methyl- 2-hexynyl, 1-heptynyl, 2-heptynyl, 3-heptynyl 4-heptynyl, 1-methyl- 4-heptynyl, 3-methyl-1-heptynyl, 3-methyl- 2-heptynyl 1-octynyl, 2-octynyl or 3-octynyl.

Aryl refers to a radical derived from an aromatic hydrocarbon atom such as phenyl, methylphenyl, dimethylphenyl, α-naphthyl, β-naphthyl, biphenyl, or anthryl.

Cycloalkyl refers to a radical of a saturated cyclic hydrocarbon such as cyclopropyl, cyclobutyl, cyclopentyl, cyclohexyl, cycloheptyl, cyclooctyl or adamantyl.

Halogen refers to a radical of fluorine, chlorine, bromine or iodine.

Unless otherwise indicated, in the above description and throughout this document, the parenthetical term ($C_n-C_m$) is inclusive such that a compound of ($C_1-C_4$) would include compounds of 1, 2, 3 and 4 carbons and their isomeric forms.

It will be apparent to those skilled in the art that compounds of this invention may exist in different tautomeric forms. The scope of this invention includes all tautomeric forms in addition to those represented in the formulas used herein. It will also be apparent to those skilled in the art that compounds of this invention may contain several chiral centers. The scope of this invention includes all enantiomeric or diastereomeric forms of Formula I compounds either in pure form or as mixtures of enantiomers or diastereomers. Specifically, the azetidinones of this invention have chiral carbon atoms at positions $C_3$ and $C_4$ of the β-lactam ring and at position $C_4$ in the pyrazolidinone ring. In the β-lactam ring, the preferred orientation is cis at centers 3 and 4 and the preferred stereochemistry at $C_3$ and $C_4$ is 3(S) and 4(S). The phrase "cis at centers 3 and 4" means that the substituents at C-3 and C-4 are both oriented on the same side of the β-lactam ring.

The scope of this invention includes the pharmaceutically acceptable acid salts of the disclosed compounds. Acid salts are formed by reacting the compounds described herein with the appropriate acid in a suitable solvent. Suitable acids for this purpose include hydrochloric, sulfuric, phosphoric, hydrobromic, hydroiodic acetic, lactic, citric succinic, benzoic, salicylic palmoic cyclohexansulfamic, methanesulfonic, naphthalenesulfonic, p-toluenesulfonic, or maleic.

The scope of this invention includes the pharmaceutically acceptable salts of the disclosed compounds. Such salts include the following cations but are not limited to these: alkali metal ions such as potassium, sodium, lithium, alkaline earth metal ions such as magnesium or calcium and ammonium ions such as ammonium, tetralkylammonium and pyridinium. Metal salts are formed by suspending the compounds in water or other suitable solvent and adding a dilute metal base such as sodium or potassium bicarbonate until the pH is between 6 and 7.

The compounds of this invention and their respective pharmaceutically acceptable salts have antibiotic activity against a variety of gram-negative bacteria including *Escherichia coli, Klebsiella pneumoniae* and *Pseudomonas aeruginosa*. The compounds are useful for treating bacterial infections in animals, including and most preferably humans. Compounds of the invention are tested for in vitro antimicrobial activity using standard testing procedures such as the determination of minimum inhibitory concentration (MIC) by methods described in "Methods for Dilution Antimicrobial Susceptibility Tests for Bacteria That Grow Aerobically" (M7-A) Published December 1985 by the National Committee for Clinical Laboratory standards, 771 East Lancaster Avenue, Villanova, Pa., 19084. Briefly, MIC values are determined in unsupplemented Mueller Hinton Agar (MHA). The compounds tested are diluted serially into molten MHA at 47° C. The agar is poured into petri dishes and allowed to harden. The various bacteria used for testing are grown overnight on MHA at 35° C. and transferred to Tryptiease Soy Broth (TSB) until a turbidity of 0.5 McFarland standard is obtained. The bacteria are diluted one to twenty in TSB and inoculated on the plates (1 $\mu$l using a Steers replicator). The plates are incubated at 35° C. for 20 hours and the MIC is read to be the lowest concentration of drug that completely inhibits visible growth of the bacterium. The MIC test results of four typical compounds of this invention. Compounds 60(b) 60(d) 60(m) and 60(p) are given in Tables I and II.

Various compositions of the present invention are presented for administration to humans and animals in unit dosage forms, such as tablets capsules, pills powders, granules sterile parenteral solutions or suspensions eye drops solutions or suspensions, and emulsions containing suitable quantities of compounds of Formula I.

For oral administration solid or fluid unit dosage forms can be prepared. For preparing solid compositions, the compounds of this invention are mixed with conventional ingredients such as talc magnesium stearate dicalcium phosphate, magnesium aluminum silicate, calcium sulfate, starch, lactose, acacia, methylcellulose, and/or functionally similar pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

For preparing fluid compositions, the compounds of this invention are dissolved in an aqueous vehicle together with sugar, aromatic flavoring agents and preservatives to form a syrup. An elixir is prepared by using a hydroalcoholic vehicle such as ethanol, suitable sweeteners such as sugar and saccharin, and aromatic flavoring agents. Suspensions are prepared in an aqueous vehicle with the aid of a suspending agent such as acacia, tragacanth, or methylcellulose.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compounds of Formula I may also be administered in a carrier suitable for topical administration, such carriers include creams, ointments, lotions, pastes, jellies, sprays, aerosols, bath oils, or other pharmaceutical carriers which accomplish direct contact between the compound and the surface of the skin area to be treated. In general pharmaceutical preparations may comprise from about 0.01% to about 10%, and preferably from about 0.1% to about 5% by w/w of the active compound in the suitable carrier.

Additionally, a rectal suppository can be employed to deliver the active compound. This dosage form is of particular interest where the mammal cannot be treated conveniently by means of other dosage forms, such as orally or by insufflation, as in the case of young children or debilitated persons. The active compound can be incorporated into any of the known suppository bases by methcds known in the art. Examples of such bases include cocoa butter, polyethylene glycols (carbowaxes), polyethylene sorbitan monostearate, and mixtures of these with other compatible materials to modify the melting point or dissolution rate. These rectal suppositories can weigh from about 1 to 2.5 g.

The term "unit dosage form", as used in the specification, refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the novel unit dosage forms of this invention are dictated by and directly dependent on the unique characteristics of the active material and the particular effect to be achieved and the limitations inherent in the art of compounding such an active material for use in humans and animals as disclosed in detail in this specification, these being features of the present invention. Examples of suitable unit dosage forms in accord with this invention are tablets, capsules, pills, suppositories, powder packets, wafers granules, cachets, teaspoonfuls, tablespoonfuls, drops, ampules, vials, aerosols with metered discharges, segregated multiples of any of the foregoing, and other forms as herein described.

An effective quantity of the compound is employed in treatment. The dosage of the compound for treatment depends on many factors that are well known to those skilled in the art. They include for example, the route of administration and the potency of the particular compound. A dosage schedule for humans having an average weight of 70 kg is from about 50 to about 3000 mg of compound in a single dose. More specifically, the single dose is from about 100 mg to 2000 mg of compound. Typically the dosages are given one to four times per day.

The process for making compounds of Formula I is illustrated in Charts A, B, and C. The requirements for protecting groups in the processes of Charts A and B are well recognized by one skilled in the art of organic chemical synthesis and suitable protecting groups are used in the processes disclosed herein. It is recognized that conditions for introduction and removal of protecting groups should not detrimentally alter any other groups in the molecule.

Examples of suitable nitrogen protecting groups are:
(1) benzyl;
(2) triphenylmethyl (trityl);
(3) trialkylsilyl, such as trimethylsilyl or t-butyldimethylsilyl;
(4) t-butoxycarbonyl (t-BOC or BOC);
(5) benzyloxycarbonyl (Cbz);
(5) trifluoroalkanoyl, such as trifluoroacetyl or trifluoropropionyl; or
(7) diphenyl(methyl)silyl.

Introduction and removal of such nitrogen protecting groups are well known in the art of organic chemistry: See, for example, (1) J. F. W. McOmie, Advances in Organic Chemistry, Vol. 3, pages 191-281 (1963); (2) R. A. Boissonas, Advances in Organic Chemistry, Vol. 3, pages 159-190 (1963); (3) "Protective Groups in Organic Chemistry:, J. F. W. McOmie, Ed., Plenum Press, New York, 1973, pp 74, and (4) "Protective Groups in Organic Synthesis", Theodora W. Greene, John Wiley and Sons, New York, 1981.

Under certain circumstances it may be necessary to protect two or more nitrogen atoms with different protecting groups allowing selective removal of one protecting group while leaving the remaining protecting groups in place. For example, the Cbz group can be selectively removed in the presence of the BOC group and vice versa.

The compounds of this invention are prepared by the procedures outlined in Charts A, B, and C The substituents at the $C_4$ position in the $\beta$-lactam ring defined by $R_1$ and $R_2$ are prepared by procedures outlined in Chart A. The starting compound cis-($\pm$)-4-(methoxycarbonyl)-3-[[(benzyloxy)carbonyl]amino]-2-azetidinone, A-1, is known. J. Org. Chem., 2765-2767 (1982). The trans compound is known or is made by known methods. Thus compound A-1 is either cis or trans with respect to the substituents on $C_3$ and $C_4$. It is recognized that alternative protecting groups could be used in place of the benzyloxycarbonyl group of compound A-1. See also, W. F. Huffman et al., J. Am. Chem. Soc., 2352 (1977); D. B. Bryan et al., J. Am. Chem. Soc., 2353 (1977).

The $C_4$-carbomethoxy group of compound A-1, is reduced to the $C_4$-hydroxymethyl group of compound A-2, by use of metal hydride reducing reagents, such as sodium borohydride or zinc borohydride, in ether solvents, such as diethyl ether or tetrahydrofuran, at a temperature range of 0° to 80° C. The product is obtained after a normal aqueous work-up procedure followed by column chromatography on silica gel.

The hydroxymethyl group of compound, A-2, reacts with $HO_2CCH_2$—$NHR_4$, wherein $R_4$ is —CHO or —BOC, to produce compound A-4 using approximately equimolar quantities of the acid, 1-hydroxy-1-benzotriazole (HOBT), and a carbodiimide, such as dicyclohexylcarbodiimide (DCC) or diisopropylcarbodiimide (DIC) and a catalytic amount of 4-dimethylaminopyridine. The choice of solvents is methylene chloride, dimethylformamide or a combination of both solvents and the reaction is carried out in general at the temperature range of 0° C. to ambient temperature. The desired compound is obtained after filtration of precipitated dicyclohexylurea, removal of HOBT by washing with aqueous sodium bicarbonate solution, and column chromatography on silica gel.

To prepare compounds represented by A-3, the hydroxymethyl compound, A-2, reacts with a suitable protected chloroformate ester of formula $ClCO_2R_5$ where $R_5$ is —($C_1$-$C_8$)alkyl, —$(CH_2)_2NHBOC$, —$(CH_2)_2$—$N(CH_3)BOC$, —$(CH_2)_2OC(O)NH_2$, —$(CH_2)_2Cl$, —$(CH_2)_2OCH_3$ or —$(CH_2)_2NHC(O)H$, to give the compound, A-3. The reaction conditions involve the use of an inert solvent such as methylene chloride tetrahydrofuran, or dimethylformamide at $-20°$ C. to 30° C. in the presence of a slight excess of organic base, such as pyridine, 2,4-lutidine, or triethylamine. Following extractive workups involving successive washes with acid and base, the products are isolated by chromatography or crystallization. Some chloroformate esters are commercially available and others can be prepared according to the teaching of Huntress, "Organic Chlorine Compounds," John Wiley and Sons Inc., New York, N.Y., 1948; F. Stain et al., J. Am. Chem. Soc., 72, 1254 (1950), H. G. Ashburm et al., J. Am. Chem Soc. 60, 2933 (1938). Briefly, the process described in these references is to contact an alcohol with an excess of phosgene either neat or in an organic solvent. An alternative process to prepare compounds represented by A-3, can be used when the desired chloroformate is unavailable. Compound A-2 is placed in a solvent such as methylene chloride, ethyl acetate, tetrahydrofuran, or acetonitrile containing a slight excess of an organic base, such as pyridine, triethylamine, or 2,4-lutidine, and is reacted at $-20°$ C. to 30° C. with a solution of phosgene in an inert solvent, such as toluene, benzene or methylene chloride. The intermediate chloroformate thus formed is not isolated, but is treated with a molar equivalent of the suitably protected desired alcohol, $R_5OH$, where $R_5$ is —($C_1$-$C_8$)alkyl, —$(CH_2)_2NHBOC$, —$(CH_2)_2$—$N(CH_3)BOC$, —$(CH_2)_2OC(O)NH_2$, —$(CH_2)_2Cl$, —$(CH_2)_2OCH_3$ or —$(CH_2)_2NHCHO$, in the presence of an organic base in an inert solvent at $-20°$ C. to 30° C. to yield the compound, A-3. This alternative or reversed process is known in the field of steroid chemistry, G. Schubert et al., Die Pharmazie, 35, 453 (1980).

To prepare compounds of this invention wherein $R_1$ or $R_2$ are alkyl, alkenyl, alkynyl, cycloalkyl, optionally substituted phenyl or benzyl, or fluoroalkyl, the hydroxyl substituent in compound A-2 is converted to an appropriate leaving group, Lg, by methods known in the art to give compound, A-5. The leaving group is displaced by a known nucleophiles by methods known in the art to give compound A-6 wherein R' is alkyl, alkenyl, alkynyl, cycloalkyl, optionally substituted phenyl or benzyl or fluoroalkyl.

To prepared compounds of this invention wherein $R_1$ or $R_2$ are the same, a suitable amino acid derivative, A-7, is cyclized by known methods to give the substituted four membered ring, A-8, Slusarchyk, W. A., et al., Tetrahedron Letters, 2789-2792 (1986). Deprotection of the lactam nitrogen gives the hydroxy amide, A-9, which is reduced to the $\beta$-lactam by titanium trichloride in tetrahydrofuran and water, Miller, M. J., et al., J. Org. Chem. 1126 (1985), Miller, M. J., et al., J. Org. Chem., 410 (1980), Miller, M. J., et al., Tetrahedron, 2571 (1983). Other procedures to prepare substituted azetidinones are known in the art; see, for example, Teutsch, G., et al., Tetrahedron, 2677–2684 (1986), Teutsch, G., et al., Tetrahedron Letters, 1561–1562 (1984), and U.S. Pat. No. 4,478,749, column 19, lines 1–40.

Optically active compounds of Formula I are prepared by the use of the appropriate optically active form of compound, A-1, which is prepared by known methods, Takeda European patent application 8310461-3. The resolving agents are any of the known resolving agents such as optically active camphorsulfonic acid, bis-o-toluoyltartaric acid, tartaric acid, and diacetyl tartaric acid which are commercially available and which are commonly used for resolution of amines. See Organic Synthesis, Coll. Vol. V., p. 932 (1978) which describes the resolution of R-(+) and S-(−)-α-phenyl-ethylamine with (−)-tartaric acid.

The preferred starting compound for making optically active compounds of Formula I, cis-(±)-1-[(2',4'-dimethoxyphenyl)methyl]-4-(methoxycarbonyl)-3-phanylmethoxycarboxyamino-2-azetidinone, is known, Chem. Pharm. Bull., 2646–2659 (1984). The $C_3$ protecting group is removed by hydrogenolysis to produce the corresponding free amine. An appropriate substituted tartaric acid enantiomer is then added such as (+)-di-p-toluoyl-D-tartaric acid and reaction conditions altered to facilitate precipitation of the appropriate azetidinone diastereomeric salt. The tartaric acid is removed by treating the compound with inorganic base such as aqueous sodium bicarbonate to produce the desired resolved amino-azetidinone.

The procedures used to prepare the substituted pyrazolidonylaminocarbonylheterocycle portion of the compounds of this invention are also outlined in Chart A. This segment of the compound is prepared by coupling a suitable pyrazolidinone, A-20, to a protected pyridinone carboxylic acid, A-21. The coupling reaction is done in a suitable solvent such as DMF, in the presence of HOBT and DCC or DIC at ambient temperatures. The coupled product, A-22, is purified by column chromatography, recrystallization or methods known to those skilled in the art. The protecting group on the pyrazolidinone is readily removed by methods well known in the art to give the aminopyrazolidinone, A-23.

Pyrazolidinones represented by A-20 are prepared from serine when $R_6$ or $R_7$ are hydrogen or from threonine when one of $R_6$ or $R_7$ is methyl as outlined in Chart C. The stereochemistry at the $C_4$ position of the pyrazolidinone ring is determined by the use of either D or L, serine or threonine, as the starting material. The amino acid is protected with a t-butoxycarbonyl group using procedures well known in the art to give compound C-2. The protected amino acid reacts with tosyl chloride in pyridine to give the tosyl ester, C-3, which cyclizes in the presence of hydrazine to give the desired pyrazolidinone, A-20, which is purified by column chromatography, recrystallization or methods known to those skilled in the art.

Alternative procedures to complete the rest of the molecule are outlined in Chart B. As shown in Chart B, the benzyloxycarbonyl group of compound B-1, is removed by catalytic hydrogenolysis using palladium metal supported on carbon or palladium metal itself under a hydrogen gas atmosphere in suitable solvents such as alcoholic solvents, ether solvents or ethyl acetate, at ambient temperature. The compound, B-2, is obtained by removal of the solid catalyst and removal of the solvent under reduced pressure.

The $C_3$-amino group of compound, B-2, is acylated with a suitable carboxylic acid to produce compound B-3. This conversion may be carried out by any of a number of amide or peptide forming reaction sequences such as methods described in Methoden der Organischem Chemie, Vierte Auflage, Band XV/2, E. Wunch ed., Georg Thieme Verlag, Stuttgart, p. 1. A preferred acylation process is the use of approximately equimolar quantities of a desired acid, HOBT, and a carbodiimide, such as DCC or DIC. The choice of solvents is methylene chloride, dimethylformamide or a combination of both solvents and the reaction is carried out in general at the temperature range of 0° C. to ambient temperature. The desired compound is obtained after filtration of precipitated dicyclohexylurea, removal of HBOT by washing with aqueous sodium bicarbonate solution and column chromatography on silica gel if necessary. Also, the compounds can be made by other methods known in the art, see, for example, J. Am. Chem. Soc., 2401–2404 (1973).

The amide, B-3, reacts with approximately 1.2 to 1.6 equivalents of chlorosulfonyl isocyanate at −20° to 0° C. in organic solvents, such as methylene chloride, acetonitrile or a combination of both solvents to produce the activated azetidinone B-4 which is coupled to a silylated intermediate prepared by reacting N-methyl-N-(trimethylsilyl)-trifluoroacetamide or bis-(trimethylsilyl)-trifluoroacetamide with a suitable pyrazolidinonylaminocarbonylheterocycle, A-23, in organic solvents, such as acetonitrile, methylene chloride or tetrahydrofuran, at ambient temperature. The silylated intermediate reacts with compound B-4, optionally in the presence of a tertiary amine base such as 2,6-lutidine, at about 0° C. and the mixture is stirred at 0° or slowly warmed to room temperature over a period of one to 5 hours. The crude product is obtained after a normal aqueous work-up procedure and followed by purification by column chromatography. Removal of any remaining protecting groups by known methods gives the N-1-sulfonyl-aminocarbonyl compound, B-5.

Without further elaboration it is believed that one skilled in the art can, using the preceding description practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLE 1 cis-(±)-4-(Hydroxymethyl)-3-[((phenylmethoxy-carbonyl)amino]-2-azetidinone

To a stirred solution of zinc chloride (23.2 g) in anhydrous tetrahydrofuran (300 ml) at 0° C. is added sodium borohydride (13.8 g) and the mixture is allowed to warm to room temperature and is stirred overnight. To the mixture is added cis-(±)-4-(methoxycarbonyl)-3-[((phenylmethoxy)-carbonyl)amino]-2-azetidinone (39.2 g) and the reaction mixture is slowly heated to 65° C. and stirred at that temperature for 2 hours. The reaction mixture is cooled to 0° C. and 6N hydrochloric acid (200 ml) is added dropwise with stirring. The mixture is poured into ethyl acetate (1 l) and the organic layer is taken. The aqueous layer is saturated with sodium chloride and reextracted with ethyl acetate (200 ml). The combined organic layer is washed with water (200 ml) and with 200 ml of brine twice and dried over anhydrous sodium sulfate. The solvent is concentrated under reduced pressure to afford a yellow oil which is purified by column chromatography on silica gel (ethyl acetate as eluent) to obtain 24.3 g of the title product. Physical characteristics are as follows:

m.p. 98°–100° C.

EXAMPLE 2 cis-(±)-3-[2-[(2-t-Butoxycarbonylamino-4-thiazolyl]-2-[(1-t-butoxycarbonylmethoxy)imino]]acetamido-4-hydroxymethyl-2-azetidinone To a stirred solution of cis-(±)-4-(Hydroxymethyl)-3-[((phenylmethoxy)-carbonyl)amino]-2-azetidinone (19.5 g) in methanol (150 ml) is added palladium black (7.6 g) slurried in ethanol (25 ml) and the reaction mixture is stirred under one atmosphere of hydrogen gas for 24 hours. Toluene (100 ml) is added to the reaction mixture and it is stirred for 15 minutes. The solid material is filtered and the filtrate solution is concentrated under reduced pressure. The residue is dissolved in methylene chloride (200 ml) and dimethylformamide (500 ml) and cooled in the ice bath. To this cooled solution 1-[(2-t-butoxycarbonylamino)-4-thiazolyl]-[(1-t-butoxycarbonylmethoxy)-imino]carboxylic acid (23.8 g) is added followed by dicyclohexylcarbodiimide (12.6 g) and 1-hydroxybenzotriazole (4.2 g). The reaction mixture is stirred for 3 hours at 0° C. The precipitated solid is filtered and the filtrate solution is partitioned between ethyl acetate (2.5 l) and water (1 l). The organic layer is taken and the aqueous layer is washed with 500 ml of ethyl acetate twice. The combined organic layer is washed with aqueous sodium bicarbonate followed by brine and dried over anhydrous sodium sulfate. It is filtered and the filtrate solution is concentrated under reduced pressure and the residual material is chromatographed on silica gel eluting with 1:1::hexane:ethyl acetate and ethyl acetate to obtain 14.1 g of the title compound. Physical characteristics are as follows:

m.p.: 195° C. (decomp.)

EXAMPLE 3 cis-(±)-3-[2[(2-t-Butoxycarbonylamino-4-thiazolyl]2-[(1-t-butoxycarbonylmethoxy)imino]]acetamido-4-N-formyl-glycinoyloxymethyl-2-azetidinone To a mixture of cis-(±)-3-[2[(2-t-Butoxycarbonylamino-4-thiazol-yl]2-[(1-t-butoxycarbonylmethoxy)imino]]acetamido-4-hydroxymethyl-2-azetidinone (4.5 g), 1-hydroxybenzotriazole (1.216 g), dimethylaminopyridine (122 mg), N-formylglycine (1.62 g) and in the presence of a small amount of 4A molecular sieves in 60 ml of methylene chloride and 6 ml of dimethylformamide, dicyclohexylcarbodiimide (3.25 g) is added with stirring at room temperature. The reaction is complete in 2 hours. The precipitated solid is filtered off, washed with methylene chloride (50 ml) and the filtrate solution is stirred with aqueous sodium bicarbonate (1.89 g sodium bicarbonate in 40 ml water) at room temperature for 15 minutes. The organic layer is taken, dried over sodium sulfate and concentrated under reduced pressure. The residue is passed through the medium pressure silica gel column eluting with 3:1::hexane:ethyl acetate and ethyl acetate to obtain 3.6 g of the title compound. Physical characteristics are as follows:

m.p.: 108°–110° C.

EXAMPLE 4

Alternative preparation of cis-(±)-4-(Hydroxy-methyl)-3-[(phenylmethoxy)carbonyl)amino]-2-azetidinone A solution of 1.63 g of sodium borohydride in 25 ml of water is added dropwise to a well stirred solution of 3.0 g of cis-(±)-4-(methoxycarbonyl)-3-[(phenylmethoxy)carbonyl)amino]-2-azetidinone in tetrahydrofuran (190 ml). The addition is made over a period of 10 minutes while stirring in an ice bath. The reaction is stirred for 3 hours. Methylene chloride (250 ml) is added followed by anhydrous sodium sulfate. A clear solution is obtained by filtration. The solvent is removed and the residue is dissolved in acetone. The solution is clarified by filtration and concentrated to give 2.84 g of the title compound. Physical characteristics are as follows:

$^{13}C$ NMR ($\delta$, $CH_3OH$-$d_6$): 55.9, 60.2, 61.6, 67.9, 128.7–129.3, 137.6, 158, 170.7.

EXAMPLE 5 cis-(±)-4-[Methoxycarbonyl)oxymethyl]-3-[((phenylmethoxy)-carbonyl)amino]-2-azetidinone Methyl chloroformate (2.42 g) is added dropwise to a solution of 3.2 g of cis-(±)-4-(Hydroxymethyl)-3-[((phenylmethoxy)carbonyl)-amino]-2-azetidinone and 3.03 g of pyridine in 100 ml of methylene chloride while stirring at 0° C. After one hour an additional 0.5 g of methyl chloroformate is added. The reaction mixture is stirred an additional 0.5 hour and then washed successively with dilute mineral acid (e.g., HCl or $H_2SO_4$), water and potassium bicarbonate solution. Evaporation of the solvent and trituration of the residue with ethyl acetate affords 2.48 g of the title compound. Physical characteristics are as follows:

m.p.: 155°–158° C.

According to the procedures of Example 5, the following compounds are also prepared:

cis-(±)-4-[(Formylaminoethoxycarbonyl)oxymethyl]-3-[((phenylmethoxy)carbonyl)amino]-2-azetidinone;

cis-(±)-4-[(t-Butoxycarbonylaminoethoxycarbonyl)oxymethyl]-3-[((phenylmethoxy)carbonyl)amino]-2-azetidinone;

cis-(±)-4-[(Aminocarbonyloxyethoxycarbonyl)oxymethyl]-3-[((phenylmethoxy)carbonyl)amino]-2-azetidinone; and cis-(±)-4-[(Chloroethoxycarbonyl)oxymethyl]-3-[((phenylmethoxy)carbonyl)amino]-2-azetidinone.

EXAMPLE 6 cis-(±)-1-[(Chlorosulfonyl)aminocarbonyl)-4-[(methoxycarbonyl)oxymethyl]-3-[((phenylmethoxy)carbonyl)amino]-2-azetidinone Chlorosulfonyl isocyanate (175 mg) is added dropwise to a suspension of 382 mg of cis-(±)-4-[Methoxycarbonyl)oxymethyl]-3-[((phenylmethoxy)carbonyl)amino]-2-azetidinone in 8 ml of methylene chloride while stirring in an ice bath. The bath is removed after 20 minutes and the mixture stirred at ambient conditions. Evaporation of the solvent under vacuum leaves the title compound as a glass which is used without purification.

According to the procedure of Example 6, the following chlorosulfonyl compounds are also prepared:

cis-(±)-1-[(Chlorosulfonyl)aminocarbonyl]-4-[(formylaminoethoxycarbonyl)oxymethyl] 3-[((phenylmethoxy)carbonyl)amino]-2-azetidinone;

cis (±)-1-[(Chlorosulfonyl)aminocarbonyl]-4-[t-butoxycarbonylaminoethoxycarbonyl)oxymethyl]-3-[((phenylmethoxy)carbonyl)amino]-2-azetidinone;

cis-(±)-1-[(Chlorosulfonyl)aminocarbonyl]-4-[(aminocarbonyloxyethoxycarbonyl)oxymethyl]-3-[((phenylmethoxy)carbonyl)amino]-2-azetidinone; and cis (±) 1-[(Chlorosulfonyl)aminocarbonyl]-4-[(chloroethoxycarbonyl)oxymethyl]-3-[((phenylmethoxy)carbonyl)amino]-2-azetidinone.

EXAMPLE 7 t-Butylcarbamoyl-L-serinemethyl ester-p-toluenesulfonate

Triethylamine (22.4 ml) is added to a heterogeneous mixture of L-serinemethyl ester hydrochloride salt (25 g) in methylene chloride (300 ml) with stirring and the resulting solution is cooled in an ice bath. t-BOC anhydride (25 g) is slowly added and the reaction mixture is stirred at 0° C. for one hour. The mixture is warmed to room temperature and additional t-BOC anhydride (5 g) is added. After 1.5 hours at room temperature the mixture is cooled in an ice bath and pyridine (19.5 ml) is added followed by tosylchloride (37 g). The mixture is kept at 0° C. for 4 days. The mixture is washed with additional methylene chloride (300 ml) and water (300 ml) and the organic layer is washed with water (2×200 ml), dried over sodium sulfate, and concentrated under reduced pressure. The residue is passed through a column of silica gel eluting with 3:1::hexane:ethyl acetate followed by 1:1::hexane:ethyl acetate to obtain the title compound (35 g). Physical characteristics are as follows:

m.p.: 71°–73°.

EXAMPLE 8

4(S)-t-Butylcarbamoylpyrazolidinone

Hydrazine (9.6 g, 300 mm) is added to a solution of t-butylcarbamoyl-L-serine methyl ester-p-toluenesulfonate at 0° C. in methylene chloride (350 ml) with stirring. After 30 minutes the ice bath is removed and the mixture is kept at room temperature overnight. The mixture is concentrated and the residue is passed through a column of silica gel eluting with 1:2::ethyl acetate:methylene chloride, 1:1::-ethyl acetate:methylene chloride, and then 5% methanol in methylene chloride followed by 10% methanol in methylene chloride to give the title compound (13 g). Physical characteristics are as follows:

m.p.: 175°–178°.

EXAMPLE 9

(3-Benzyloxy-4-pyridon-6-yl)-1-carbonyl-4(S)-t-butylcarbamoylpyrazolidinone

Diisopropylcarbodiimide (6 ml) is added to a heterogeneous mixture of S-t-butylcarbamoylpyrazolidinone (5.2 g), 3-benzyloxy-4-pyridonecarboxylic acid (6.34 g) and HOBT (3 5 g) in anhydrous dimethylformamide (80 ml) at 0° C. with stirring. After 30 minutes the ice bath is removed and the mixture is stirred at room temperature for 6.5 hours. The solvent is evaporated and methylene chloride (200 ml) and aqueous sodium bicarbonate solution (2.4 g) are added to the residue and stirred for one hour. The mixture is kept at room temperature overnight, filtered, washed with water (20 ml) and methylene chloride (120 ml) and dried to give the title compound (7.8 g). Physical characteristics are as follows:

m.p.: starts to decompose at 220° and does not melt completely up to 280°.

EXAMPLE 10

(3-Benzyloxy-4-pyridon-6-yl)-1-carbonyl-4(S)-aminopyrazolidinone

Trifluoroacetic acid (15 ml) is added to (3-benzyloxy-4-pyridon-6-yl)-1-carbonyl-4(S)-t-butylcarbonylpyrazolidinone (7.0 g) in methylene chloride (15 ml) at 0° C. After 15 minutes the ice bath is removed and the mixture is kept at room temperature for one hour. The mixture is concentrated and triturated with ethyl acetate and a small amount of methylene chloride. The residue is filtered and dissolved in water (25 ml). Sodium bicarbonate solid is added to the solution until the pH is 7. The produce is filtered washed with water and dried to give the title compound. Physical characteristics are as follows:

m.p.: starts to decompose at 210° and does not melt completely up to 280°.

According to procedures of Example 10, the following compounds are also prepared:

(3-Benzloxy-4-pyridon-6-yl)-1-carbonyl-5-methyl-4(R)-aminopyrazolidinone.

Physical characteristics are as follows:

m.p.: 167°-168° C.

(3-Benzloxy-4-pyridon-6-yl-1-carbonyl-5-methyl-4(S)-aminopyrazolidinone.

Physical characteristics are as follows:

m.p.: 217°-219° C. sublimes.

EXAMPLE 11

3(S)-3-[2-(2-Amino-4-thiazoyl)-Z-(2)-(carboxyisopropyloxyimino)acetamido]-1-[(3-hydroxy-4-pyridon-6-yl)-1-carbonyl-pyrazolidinone-4-(S)-amino]-sulfonylamino-carbonyl-2-azetidinone (60(b))

Chlorosulfonylisocyanate (220 ml) is added to a heterogeneous mixture of 3-(S)-3-[2-(2-t-butyloxycarbonylamino-4-thiazoyl)-Z-(2)-t-butyloxycarbonylisopropyloxyimino)acetamido]azetidine-2-one (1.0 g) in methylene chloride (15 ml) at −40° C. and the mixture is slowly warmed to 0° C. over 90 minutes. In a separate flask, N-methyltrifluorosilyl acetamide (1.5 ml) is added to a mixture of (3-benzyloxy-4-pyridon-6-yl)-1-carbonyl-4(S)-aminopyrazolidinone (660 mg) in tetrahydrofuran (15 ml) at room temperature. After 1.5 hours, the silylated reaction mixture is added to the chlorosulfonyl isocyanate reaction mixture at −20° C. and the resulting mixture is slowly warmed to 0° C. After 5 hours, methanol (30 ml) is added and the solvent is removed. The residue is passed through a column of XAD-7 resin eluting with 15%, 30% and 50% mixtures of acetonitrile/water to give the protected intermediate.

The intermediate is debenzylated in the presence of palladium black (700 mg) under hydrogen gas (one atmosphere) in methanol (30 ml). The mixture is filtered washed with methanol and concentrated. The residue is added to a mixture of trifluoroacetic acid (30 ml) in methylene chloride (30 ml) at 0° C. and allowed to warm to room temperature. The mixture is concentrated and passed through a column of HP-20 resin eluting with water 2.5%, 5% and 7.5% mixtures of acetonitrile/water to give the title compound (65 mg).
Physical characteristics are as follows:
IR (neat) 1784, 1729 cm$^{-1}$, mass spec (FAB) 685.
According to procedures of Example 11, the following compounds are also prepared:

3(S)-3-[2-(2-Amino-4-thiazolyl)-Z-(2)(carboxyisopropyloxyimino)-acetamido]-1-[(3-hydroxy-4-pyridon-6-yl)-1-carbonyl-pyrazolidinone-4(R)-amino]-sulfonyl-aminocarbonyl-2-azetidinone (60(d))—

3(S)-3-[2-(2-amino-4-thiazolyl)-Z-(2)(carboxyisopropyloxyimino)-acetamido]-1-[(3-hydroxy-4-pyridon-6-yl) 1-carbonyl-5(S)-methyl-pyrazolidinone-4(S)-amino]-sulfonylaminocarbonyl-2-azetidinone (60(m)).

Physical characteristics are as follows:
PMR: (D$_2$O) 7.70, 7.0, 6.90, 4.90, 4.8, 3.84, 3.63, 1.38, 1.21.

3(S)-3-[2-(2-amino-4-thiazoyl)-Z-(2)-(carboxyisopropyloxyimino)-acetamido]-1-[(3-hydroxy-4-pyridon-6-yl)-1-carbonyl-5(S)-methyl-pyrazolidinone-4(R)-amino]-sulfonylaminocarbonyl-2-azetidinone (60(p)).

Physical characteristics are as follows:
PMR: (D$_2$O) 7.66, 7.2–7.1, 6.87, 5.0–4.9, 4.5, 4.0–3.8, 1.37, 1.36, 1.30.

FORMULAS

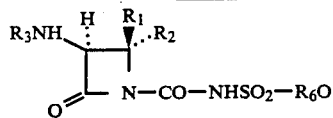

Formula I

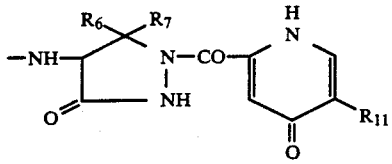

Formula II

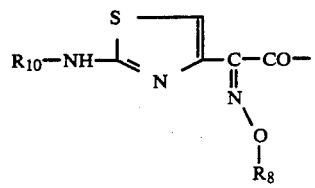

Formula III

STRUCTURE CHART

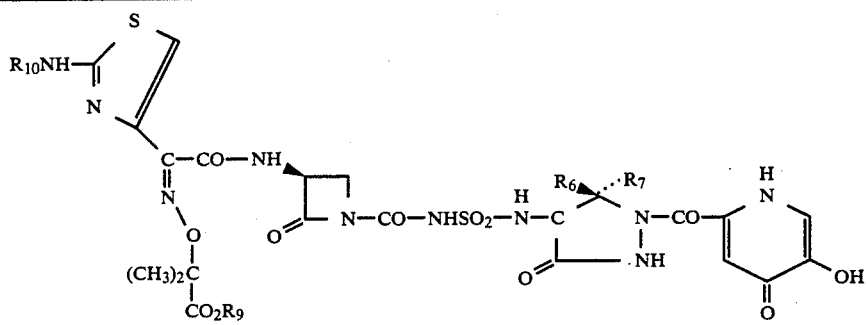

| Compound Number | C | R$_6$ | R$_7$ | R$_9$ | R$_{10}$ |
|---|---|---|---|---|---|
| 60(a) | S | H | H | (CH$_3$)$_3$C | (CH$_3$)$_3$C—O—CO— |
| 60(b) |   | H | H | H | H |
| 60(c) | R | H | H | (CH$_3$)$_3$C | (CH$_3$)$_3$C—O—CO— |
| 60(d) |   | H | H | H | H |

CHART A

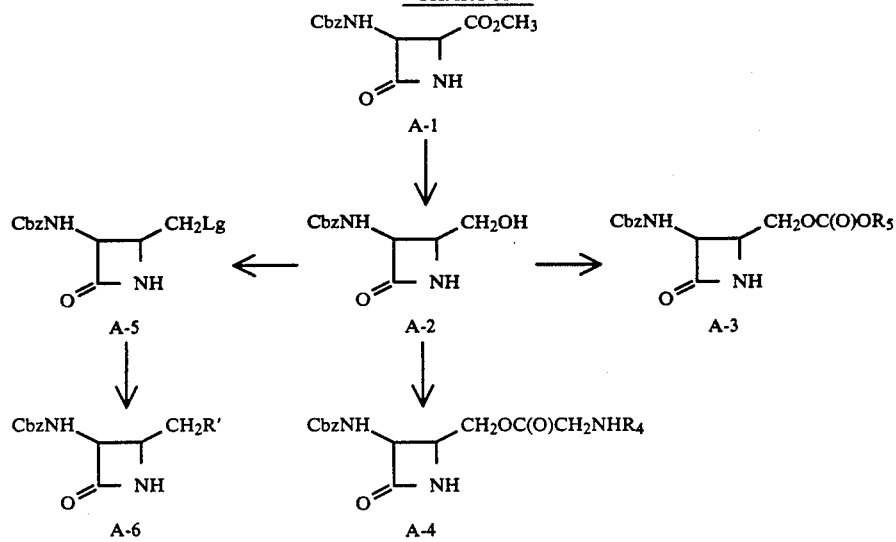

CHART A
CbzONNHC(O)CH(NH—BOC)C(R₁)(R₂)OH
A-7
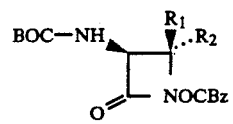
A-8
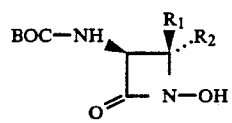
A-9
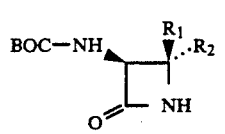
A-10
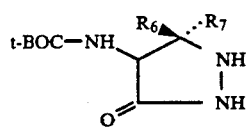
A-20
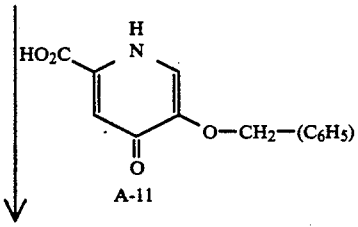
A-11
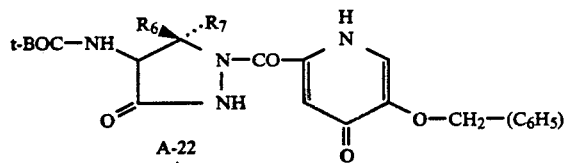
A-22
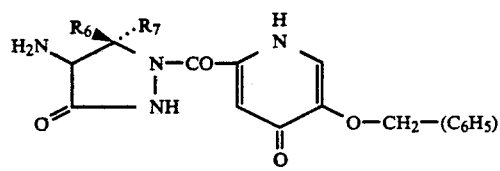

CHART B
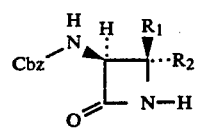
B-1
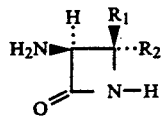
B-2
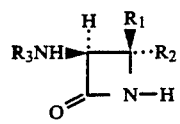
B-3
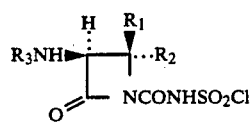
B-4
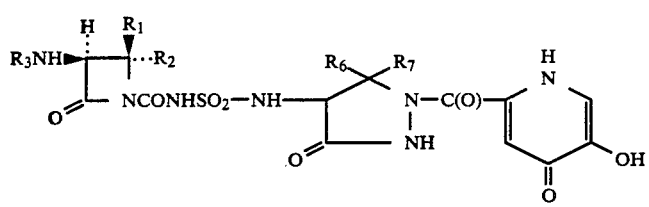
B-5
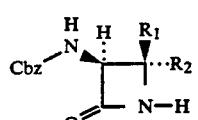
B-1
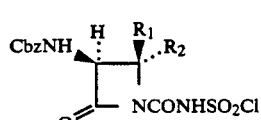
B-6

CHART B

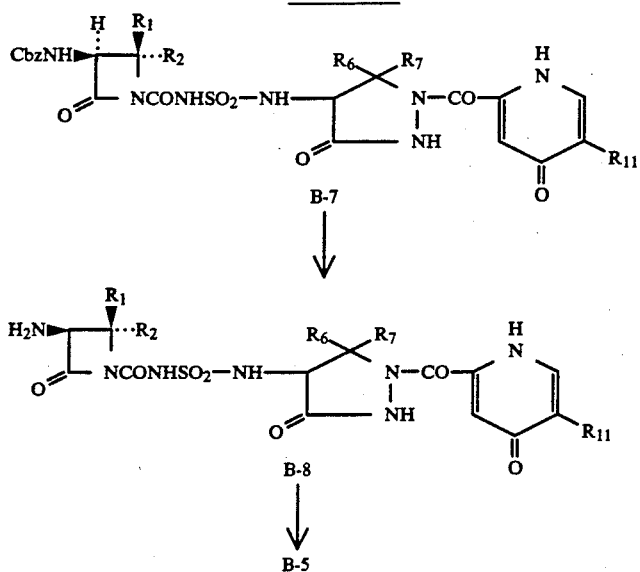

CHART C

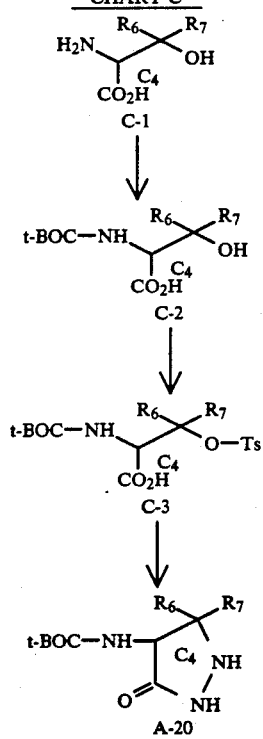

TABLE I

| | Minimum Inhibitory Concentration (μg/ml) | | |
|---|---|---|---|
| Organism | Culture Number | Compound 60(b) | Compound 60(d) |
| Staphylococcus aureus | 9218 | >64 | 64 |
| Staphylococcus aureus | 3665 | >64 | NT |
| Staphylococcus aureus | 6685 | >64 | NT |
| Staphylococcus aureus | 9213 | >64 | NT |
| Staphylococcus epidermis | 30031 | >64 | NT |
| Streptococcus faecalis | 694 | >64 | NT |
| Streptococcus pneumoniae | 41 | >64 | >64 |
| Streptococcus pyogenes | 152 | 64 | >64 |
| Citrobacter freundii | 3507 | 0.03 | 0.06 |
| Enterobacter cloacae | 9381 | 8 | 4 |

TABLE I-continued

| | Minimum Inhibitory Concentration (μg/ml) | | |
|---|---|---|---|
| Organism | Culture Number | Compound 60(b) | Compound 60(d) |
| Enterobacter cloacae | 9382 | 1 | 1 |
| Escherichia coli | 9379 | <0.008 | 0.015 |
| Escherichia coli | 9380 | <0.008 | <0.008 |
| Escherichia coli | 9451 | <0.008 | 0.015 |
| Klebsiella oxytoca | 9383 | 0.125 | 0.125 |
| Klebsiella oxytoca | 9384 | 0.06 | 0.125 |
| Klebsiella pneumoniae | 58 | 0.5 | 0.5 |
| Proteus vulgaris | 9679 | 0.06 | 0.06 |
| Serratia marcescens | 6888 | 0.03 | 0.03 |
| Pseudomonas aeruginosa | 231 | 0.25 | 0.25 |
| Pseudomonas aeruginosa | 9191 | 0.25 | 0.125 |
| Pseudomonas aeruginosa | 6676 | NT | 2 |
| Acinetobacter sp. | 30278 | NT | 1 |

NT = No test
60(b) is 3(S)-3-[2-(2-amino-4-thiazoyl)-Z-(2)-(carboxyisopropyloxyimino)acetamido]-1-[(3-hydroxy-4-pyridon-6-yl)-1-carbonyl-pyrazolidinone-4(S)-amino]-sulfonylaminocarbonyl-2-azetidinone.
60(d) is 3(S)-3-[2-(2-amino-4-thiazoyl)-Z-(2)-(carboxyisopropylimino)acetamido]-1-[(3-hydroxy-4-pyridon-6-yl)-1-carbonyl-pyrazolidinone-4(R)-amino]-sulfonylaminocarbonyl-2-azetidinone.

TABLE II

| | Minimum Inhibitory Concentration (μg/ml) | | |
|---|---|---|---|
| Organism | Culture Number | Compound 60(m) | Compound 60(p) |
| Staphylococcus aureus | 3665 | >64 | >64 |
| Staphylococcus aureus | 6685 | >64 | >64 |
| Staphylococcus aureus | 9213 | >64 | >64 |
| Staphylococcus aureus | 9218 | >64 | >64 |
| Streptococcus faecalis | 9217 | >64 | >64 |
| Streptococcus pneumoniae | 41 | >64 | >64 |
| Streptococcus pyogenes | 152 | >64 | >64 |
| Acinetobacter calcoaceticus | 12170 | 2 | 1 |
| Citrobacter freundii | 3507 | 0.03 | 0.06 |
| Enterobacter cloacae | 9381 | 8 | 8 |
| Enterobacter cloacae | 9382 | 2 | 2 |
| Escherichia coli | 9451 | <0.008 | 0.015 |
| Escherichia coli | 9379 | 0.03 | 0.03 |
| Escherichia coli | 9380 | <0.008 | 0.015 |
| Escherichia coli | 9952 | 0.015 | 0.015 |
| Klebsiella oxytoca | 9383 | 0.25 | 0.125 |
| Klebsiella oxytoca | 9384 | 0.06 | 0.06 |
| Klebsiella pneumoniae | 58 | 0.5 | 0.5 |
| Proteus vulgaris | 9679 | 0.06 | 0.06 |
| Serratia marcescens | 6888 | 0.06 | 0.06 |
| Pseudomonas aeruginosa | 231 | 0.125 | 0.125 |

TABLE II-continued

Minimum Inhibitory Concentration (μg/ml)

| Organism | Culture Number | Compound 60(m) | Compound 60(p) |
|---|---|---|---|
| *Pseudomonas aeruginosa* | 6676 | 0.5 | 0.25 |
| *Pseudomonas aeruginosa* | 9191 | 0.125 | 0.06 |

60(m) 3(S)-3-[2-(2-amino-4-thiazoyl)-Z-(2)(carboxyisopropyloxyimino)acetamido]-1-[(3-hydroxy-4-pyridon-6-yl)-1-carbonyl-5(S)-methylpyrazolidinone-4(S)-amino]-sulfonylaminocarbonyl-2-azetidinone.

60(p) 3(S)-3-[2-(2-amino-4-thiazoyl)-Z-(2)-(carboxyisopropyloxyimino)acetamido]-1-[(3-hydroxy-4-pyridon-6-yl)-1-carbonyl-5(S)-methylpyrazolidinone-4(R)-amino]-sulfonylaminocarbonyl-2-azetidinone.

I claim:

1. A compound of the formula

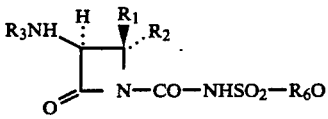

and pharmacologically acceptable salts thereof;
wherein $R_1$ and $R_2$ are the same or different and are
 a) hydrogen,
 b) $(C_1-C_{12})$ alkyl,
 c) $(C_2-C_8)$ alkenyl,
 d) $(C_2-C_8)$ alkynyl,
 e) $(C_3-C_{10})$ cycloalkyl,
 f) phenyl optionally substituted with from one to 3 substituents selected from the group consisting of halogen, hydroxy, amino, nitro, $(C_1-C_4)$alkyl, and $(C_1-C_4)$alkoxy,
 g) benzyl optionally substituted with from one to 3 substituents selected from the group consisting of halogen, hydroxy, amino, nitro $(C_1-C_4)$alkyl, and $(C_1-C_4)$alkoxy,
 h) $—CH_2—O—CO—CH_2—NHR_4$,
 i) $—CH_2—O—CO_2—R_5$,
 j) $—CH_2F$, or
 k) $—CHF_2$;
wherein $R_4$ is hydrogen, —CHO or $—CO—O—C(CH_3)_3$;
wherein $R_5$ is $(C_1-C_8)$alkyl, $—(CH_2)_2NH—CO—O—C(CH_3)_3$, $—(CH_2)_2N(CH_3)—CO—O—C(CH_3)_3$, $—(CH_2)_2OC(O)NH_2$, $—(CH_2)_2Cl$, $—(CH_2)_2OCH_3$ or $—(CH_2)_2—NHCHO$;
wherein $R_3$ is an acyl group derived from a carboxylic acid;
wherein $R_{60}$ is a pyrazolidinone of the formula;

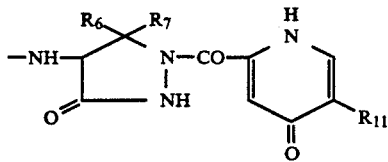

wherein $R_6$ is hydrogen or methyl;
wherein $R_7$ is hydrogen or methyl;

wherein $R_{11}$ is hydroxy or $—O—CH_2—(C_6H_5)$;
with the proviso that $R_6$ and $R_7$ cannot both be methyl.

2. A compound of claim 1 wherein $R_3$ is an oximinoacyl moiety of the formula:

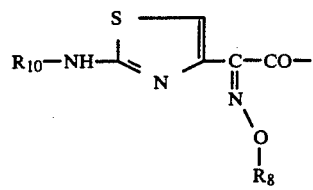

wherein $R_8$ is
 a) $—CH_3$,
 b) $—CH_2—CO_2—R_9$,
 c) $—C(CH_3)_2—CO_2—R_9$,
 d) $—CH(CH_3)—CO_2—R_9$,
 e) $—C(CH_2)—CO_2—R_9$,
 f) $—X_1—CO_2—R_9$,
 g) $—CH_2—CO—NHOH$, or
 h) $—C(CH_3)_2—CO—NHOH$;
wherein $X_1$ is 1,1-cyclopropylidene, 1,2-cyclopropylene, 1,1-cyclobutylidene 1,2-cyclobutylene, 1,3-cyclobutylene, 1,1-cyclopentylidene, 1,2-cyclopentylene, or 1,3-cyclopentylene; wherein $R_9$ is
 a) hydrogen,
 b) $(C_1-C_4)$ alkyl,
 c) $—CH(C_6H_5)_2$,
 d) $—CH_2(C_6H_5)$, or
 e) a cation;
wherein $R_{10}$ is
 a) hydrogen,
 b) $—CO—O—C(CH_3)_3$,
 c) $—CO—O—CH_2 (C_6H_5)$, or
 d) $—C(C_6H_5)_3$.

3. A compound of claim 2; wherein $R_8$ is $—C(CH_3)_2CO_2—R_9$.

4. A compound of claim 3; wherein $R_1$ and $R_2$ are hydrogen, wherein $R_9$ is hydrogen or a cation, and wherein $R_{10}$ is hydrogen.

5. A compound of claim 4; 3(S)-3-[2-(2-amino-4-thiazoyl)-Z-(2)-(carboxyisopropyloxyimino)acetamido]-1-[(3-hydroxy-4-pyridon-6-yl)-1-carbonyl-pyrazolidinone-4(S)-amino]-sulfonylaminocarbonyl-2-azetidinone or 3(S)-3-[2-(2-amino-4-thiazoyl)-Z-(2)-(carboxyisopropyloxyimino)acetamido]-1-[(3-hydroxy-4-pyridon-6-yl)-1-carbonyl-pyrazolidinone-4(R)-amino]-sulfonylaminocarbonyl-2-azetidinone.

6. A compound of claim 4; 3(S)-3-[2-(2-amino-4-thiazoyl)-Z-(2)-(carboxyisopropyloxyimino)acetamido]1-[(3-hydroxy-4-pyridon-6-yl)-1-carbonyl-5(S)-methylpyrazolidinone-4(S)-amino]-sulfonylaminocarbonyl-2-azetidinone or 3(S)-3-[2-(2-amino-4-thiazoyl)-Z-(2)-(carboxyisopropyloxyimino)acetamido]-1-[(3-hydroxy-4-pyridon-6-yl)-1-carbonyl-5(S)-methylpyrazolidinone-4(R)-amino]-sulfonylaminocarbonyl-2-azetidinone.

* * * * *